(12) United States Patent
Oxley et al.

(10) Patent No.: US 8,581,209 B2
(45) Date of Patent: Nov. 12, 2013

(54) FLUORESCENT MONITORING OF MICROCAPSULE OXIDATION

(75) Inventors: James D Oxley, San Antonio, TX (US); Jenny J. Finkbiner, Helotes, TX (US); Nitin Nitin, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 880 days.

(21) Appl. No.: 12/362,323

(22) Filed: Jan. 29, 2009

(65) Prior Publication Data

US 2010/0187439 A1 Jul. 29, 2010

(51) Int. Cl.
*G01N 21/64* (2006.01)
*B05D 3/00* (2006.01)

(52) U.S. Cl.
USPC ..... 250/459.1; 250/200; 428/403; 428/402.2; 427/331; 427/163.2

(58) Field of Classification Search
USPC ........... 250/459.1, 200; 428/3, 220, 339, 402; 427/331, 163.2, 2.13; 422/82.07, 422/82.05, 82.09
See application file for complete search history.

(56) References Cited

U.S. PATENT DOCUMENTS

| | | | |
|---|---|---|---|
| 4,001,140 A | 1/1977 | Foris et al. | |
| 5,714,121 A | 2/1998 | Alderete et al. | |
| 5,728,422 A * | 3/1998 | Kane et al. | 427/163.2 |
| 6,325,951 B1 | 12/2001 | Soper | |
| 7,252,943 B2 | 8/2007 | Griffiths et al. | |
| 2004/0058381 A1* | 3/2004 | Roitman | 435/7.1 |
| 2005/0249952 A1* | 11/2005 | Vasishtha et al. | 428/402.24 |
| 2006/0198865 A1* | 9/2006 | Freyman et al. | 424/423 |

OTHER PUBLICATIONS

Guice et al. (Proceedings of the Second Joint EMBS/BMES Conference, 2002, p. 1712-1713).*
McNamara, et al., "Optochemical Glucose Sensing in Volume Limited Samples," available at http://www.ieee.org/organizations/pubs/newsletters/leos/apr98/optochemical.htm, retrieved on Mar. 23, 2009.

* cited by examiner

*Primary Examiner* — James J Seidleck
*Assistant Examiner* — S. Camilla Pourbohloul
(74) *Attorney, Agent, or Firm* — Grossman, Tucker et al

(57) ABSTRACT

The present disclosure relates to microcapsules that include a shell material and a core material. The core material of the microcapsules contains an environmentally sensitive luminescent colorant which exhibits characteristics of an emitted wavelength bandwidth, a peak intensity for emission and a time for luminescence decay, one or more of the characteristics capable of changing upon exposure to a given environment, and a luminescent standard which exhibits characteristics of an emitted wavelength bandwidth, a peak intensity for emission and a time for luminescence decay, one or more of the characteristics do not change upon exposure to said given environment.

18 Claims, 13 Drawing Sheets

FLUORESCENT MONITORING OF MICROCAPSULE OXIDATION

FIELD OF THE INVENTION

The present disclosure relates to the incorporation of fluorescent materials into microcapsules for monitoring oxidation.

BACKGROUND

Microcapsules may be used as a delivery device for a number of substances. The microcapsules may act as a control release device, allowing for release of a given substance at a desired rate by, for example, degradation of the shell, or upon mechanical impact or application of pressure. The microcapsules may also act as a mechanism to protect certain substances sensitive to, for example, oxygen, moisture, etc. However, some amount of oxygen or moisture migration into the microcapsules may occur, which may lead to chemical changes in the core material.

A method of determining such chemical variation due to, for example, oxidation or moisture, includes sampling the microcapsules and analyzing the core ingredients by liquid or gas chromatography assays. However, such assays may take a considerable amount of time to run and portions of the sample must be destroyed. Accordingly, methods of analyzing chemical changes within the microcapsules that are relatively non-invasive and/or less time intensive may be useful.

SUMMARY OF THE INVENTION

An aspect of the present disclosure relates to microcapsules comprising a shell material and a core material. The core material may include an environmentally sensitive luminescent colorant which exhibits characteristics of an emitted wavelength bandwidth, a peak intensity for emission and a time for luminescence decay, one or more of the characteristics capable of changing upon exposure to a given environment and a luminescent standard which exhibits characteristics of an emitted wavelength bandwidth, a peak intensity for emission and a time for luminescence decay, one or more of the characteristics not changing upon exposure to said given environment.

A further aspect of the present disclosure relates to method of forming microcapsules. The method may include mixing an environmentally sensitive luminescent colorant and a luminescent standard to form a core material and encapsulating the core material in a shell material forming microcapsules. The environmentally sensitive luminescent colorant may exhibit characteristics of an emitted wavelength bandwidth, a peak intensity for emission and a time for luminescence decay, wherein one or more of the characteristics capable of changing upon exposure to a given environment. The luminescent standard may exhibit characteristics of an emitted wavelength bandwidth, a peak intensity for emission and a time for luminescence decay, wherein one or more of the characteristics do not change upon exposure to said given environment.

Another aspect of the present disclosure relates to a method of identifying changes in a core material and/or ingredient within said core material in a microcapsule, due to environmental exposure. The method may include: (i) providing microcapsules including a core material, optionally containing an ingredient, where the core material and/or ingredient's environmental sensitivity is to be monitored, wherein the microcapsule may contain an environmentally sensitive luminescent colorant exhibiting a first set of luminescent characteristics and an environmentally insensitive luminescent standard exhibiting a second set of luminescent characteristics. The method may also include (ii) measuring the first and second set of luminescent characteristics of the microcapsules at a time $t_0$ and $t_1$ in a given environment; (iii) examining the difference between the first and second sets of luminescent characteristics of the environmentally sensitive luminescent colorant and the luminescent standard; and (iv) identifying a change in the core material and/or ingredient associated with the difference in luminescent characteristics identified in step (iii).

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

The present disclosure relates to a system and method for monitoring oxidation or other chemical changes of core materials encapsulated by microcapsules via fluorescence or, more generally, luminescence. The microcapsules may incorporate an oxygen-sensitive dye core material that may alter in its fluorescent intensity upon exposure to oxygen, due to oxidation. Fluorescent spectroscopy, or other measurement techniques, may then be used to indicate or determine the degree of oxidation of the core materials within the microcapsules. Oxidation herein may be understood as the loss of electrons or hydrogen, and/or the gain of oxygen, and/or the increase in the oxidation state, of the core material.

Figure 1B:
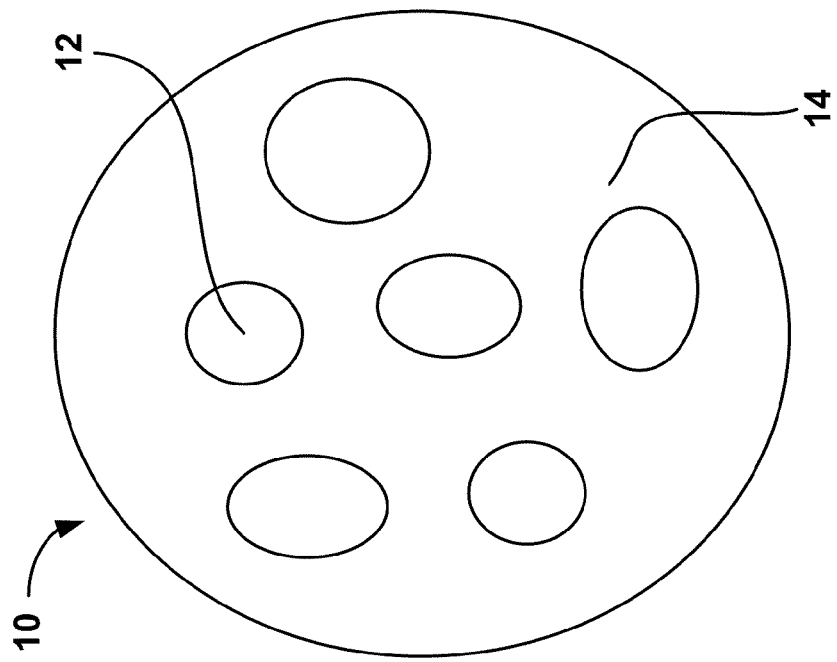
FIGS. 1a and 1b illustrates cross-sections of examples of microcapsules.
Figure 1A:
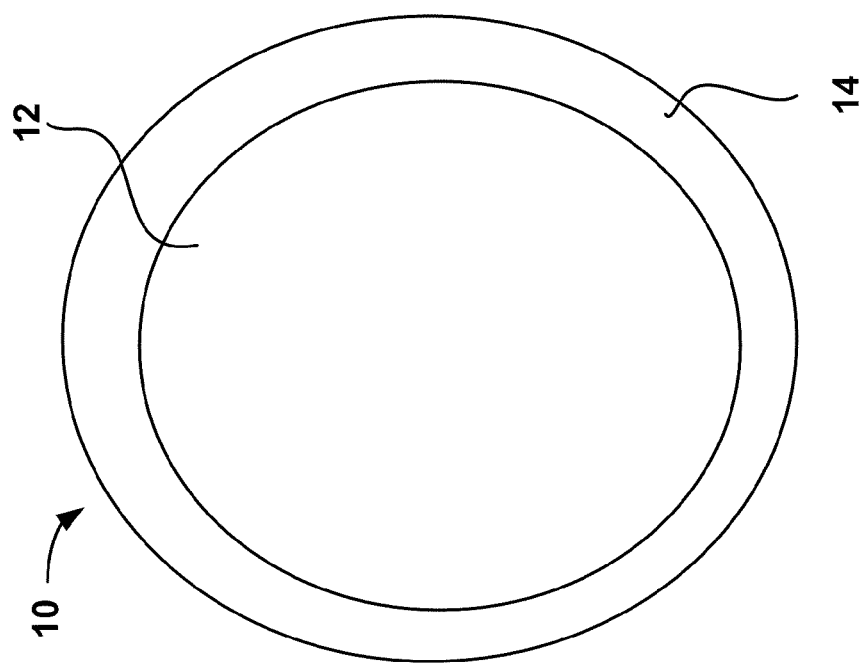

Microcapsules may generally be understood as small spheres or particles that include a core material contained or dispersed in a shell or matrix. FIG. 1a illustrates an example of the cross-section of a microcapsule 10 including a core material 12 contained within a shell material 14. FIG. 1b illustrates an example of a cross-section of a microcapsule 10 wherein the core material 12 is dispersed throughout the shell matrix 14, which forms a matrix around the domains of core material (also referred to herein as a shell).

It may be appreciated that the core material may be dispersed relatively uniformly through the microcapsule, providing a relatively uniform percent volume throughout selected portions of the microcapsules, or the core material may be dispersed relatively randomly, wherein the core material may vary by percent volume between 1 and 100 percent throughout selected portions of the microcapsules. In addition, the microcapsules need not be completely spherical in shape, i.e., maintaining the same radius about a central point, but may exhibit a number of shapes, including ellipsoid, as well as various irregular shapes.

The core material may include any material that may be advantageously provided in a microcapsule. For example the core material may include a carrier in which ingredients may be provided. The carrier may include a solvent, such as a relatively short chain hydrocarbon, such as a vegetable oil or mineral oil. The ingredients may include, for example, pharmaceuticals, flavorants, attractants (such as perfumes), colorants, etc. Pharmaceuticals may be understood as herbs, vitamins, or other natural or synthetic chemical substances utilized in the treatment, prevention, cure or diagnosis of disease or to enhance physical or mental well being. Examples of pharmaceuticals may include lutein and retinol.

Figure 2A:
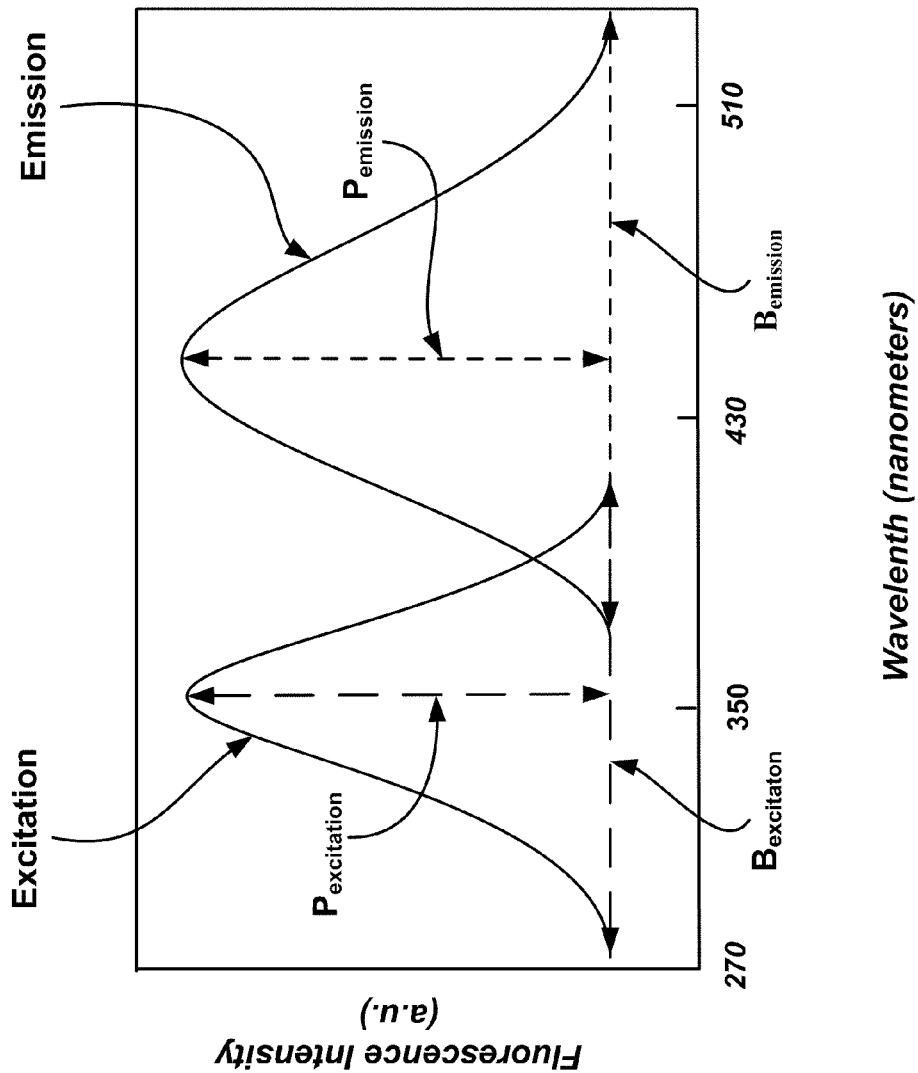
FIG. 2a illustrates an example excitation and emission spectrums for a luminescent material.
Figure 2B:
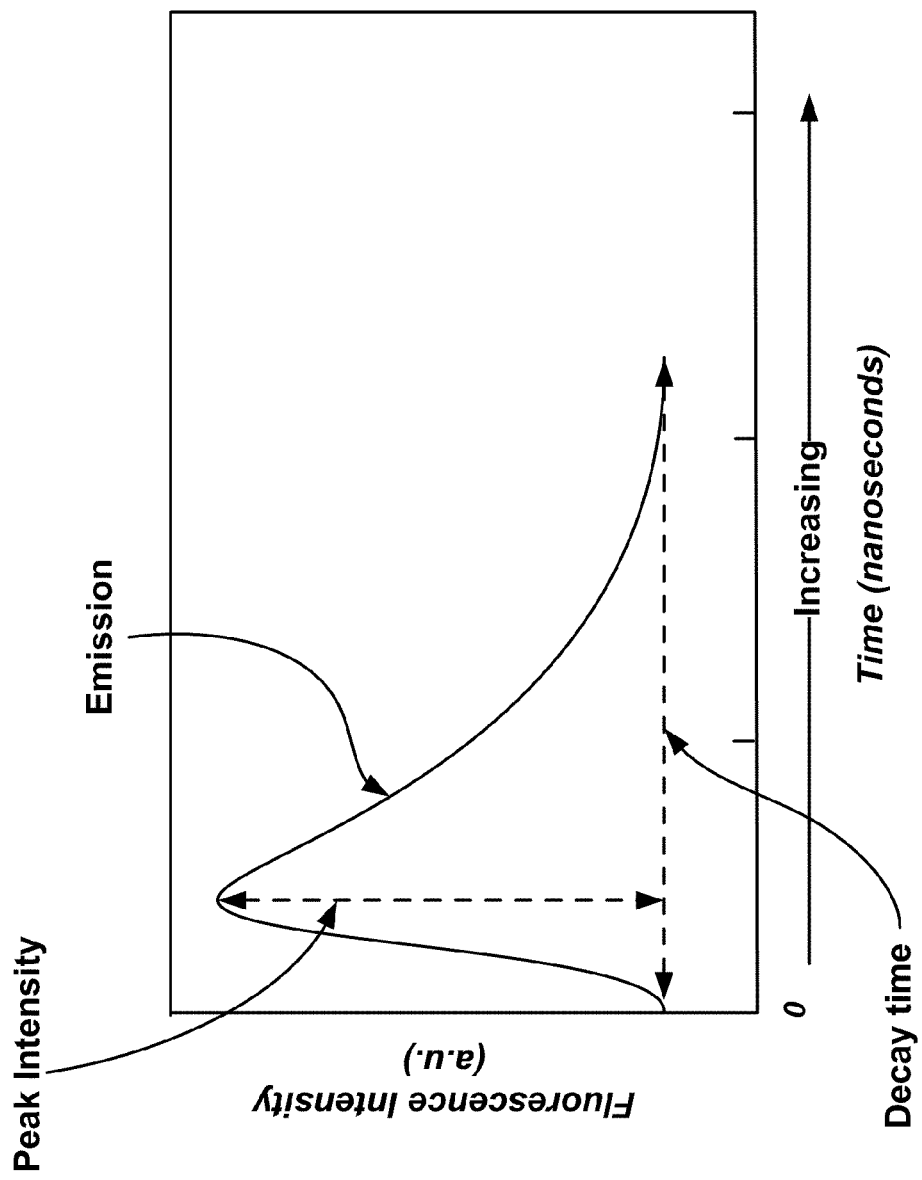
FIG. 2b illustrates an example of decay of luminescent intensity over a period of time.

As alluded to above, the present disclosure contemplates incorporating an oxygen sensitive luminescent dye or pigment (referred to herein after as colorant) to provide an indicator of oxidation of the core material and/or ingredient within the core material. Luminescence may be understood as the absorption of a portion of incident electromagnetic radiation at a first wavelength or spectrum and the emission of electromagnetic radiation at a second wavelength or spectrum. FIG. 2a illustrates an example of a given excitation wavelength spectrum of a luminescent material and a given emission wavelength spectrum of the luminescent material. Each spectrum may exhibit peak wavelengths, ($P_{excitation}$, $P_{emission}$), and band widths, ($B_{excitaton}$, $B_{emission}$), which may vary in size depending on the luminescent material and/or chemical and/or physical changes to a given luminescent material. Band width may be defined by the range of wavelengths employed for excitation or the range of wavelengths observed during emission. Furthermore, the emitted radiation may exhibit a peak intensity and a decay time, as illustrated in FIG. 2b, which may also vary depending on the luminescent material and any chemical and/or physical changes to the luminescent material.

As the colorant is exposed to oxygen and undergoes oxidation, the luminescent properties or characteristics of the colorant may be altered. For example, the span of the emitted wavelength bandwidth may change or shift in the range of +/−50 nm. Accordingly, the emitted wavelength may change or shift between +/−5 nm to 100 nm, including all values and increments therein, in 0.1 nm increments. In addition, the wavelength observed for the peak intensity for emission may similarly shift in the range of +/−50 nm, such as a shift between +/−5 nm to 50 nm, including all values and increments therein, in 0.1 nm increments. Finally, as the colorant oxidizes, the time for decay may change +/−0.5 to 5 seconds.

By contrast, the luminescent standard described herein may not be subject to such changes upon exposure to a given environmental condition (such as oxygen) individually or collectively. That is, the span of the emitted wavelength bandwidth for the standard may only change or shift in the range of less than +/−5 nm. Similarly, the wavelength observed for peak intensity for emission may only change in the range of +/−5 nm. Finally, the time for decay of the luminescent standard may only change +/−0.01 to less than 0.5 seconds.

The luminescent colorant may be selected based upon a number of factors, such as to avoid chemical interactions with the core material, shell material and/or the colorant, the food and safety requirements of the microcapsules, etc. In addition, the luminescent colorant may be chosen based on the solubility of the luminescent colorant in the core material. Where the core material may be an oil based material, the luminescent colorant may be chosen such that it may be soluble in the oil based material to improve the distribution of the colorant in the formed microcapsule. For example, the core material carrier and the luminescent colorant may be chosen such that they have Hildebrand solubility parameter values ($\delta$) that are within +/−2.0 units of one another, as measured in $(MPa)^{1/2}$. Those skilled in the art may appreciate that the Hildebrand solubility parameter represents the square root of the cohesive energy density and provides a numerical estimate of the degree of interaction of selected materials.

Furthermore, the luminescent colorant may be selected based upon the rate the colorant oxidizes. As may be appreciated, the rate of oxidation of the luminescent colorant and its changes in luminescence may be different than the rate of oxidation and change in luminescence of the oxygen sensitive core material. In such a case, one may identify a correlation. As may be appreciated, the oxidation rate of the luminescent colorant may be calibrated or otherwise compared to the oxidation rate of the other materials (e.g. ingredients) present in the microcapsule core material. Such comparison may be developed either prior to encapsulation or post-encapsulation by various testing mechanisms.

In one example the luminescent colorant may be an oxygen sensitive fluorescent dye. Fluorescent may be understood as a form of luminescence wherein molecular absorption of a photon, i.e., electromagnetic radiation, may trigger the emission of another photon with a different wavelength, such as a longer wavelength. Fluorescence may occur relatively quickly, such as in the range of 0.01 nanoseconds (ns) to a few seconds, including all values and increments therein, such as in the range of 0.01 (ns) to 10 seconds. The luminescent colorant may include, for example, ruthenium diimine complexes. In one example the luminescent colorant may also include tris(4,7-diphenyl-1,10-phenanthroline)ruthenium (II) bis(hexafluorophosphate) complex. The luminescent colorant may be present in the core material in the range of 1000 ppm or less, including all values and increments therein in 1 ppm increments, such as in the range of 1 ppm to 50 ppm.

In addition to the luminescent colorant, a luminescent standard may be utilized that may be relatively unaffected by oxidation, i.e., the standard may not be subject to oxidation. The standard may retain its luminescent properties regardless of the amount or rate of oxygen migration into the microcapsule. As may be appreciated the standard may be utilized to calibrate the measurement device with reference to changes that may occur, not only in the device itself, but also in the shell or core materials of the microcapsules as well as any slurry in which the microcapsules that may cause variation in the measurements. In addition to insensitivity to oxygen, in some examples, the luminescent standard may also be insensitive to changes in pH.

The luminescent standard may also be chosen on the basis of its solubility with other core materials. For example, the luminescent standard may be chosen such that the core material and/or the luminescent colorant have Hildebrand solubility parameter values ($\delta$) that are within +/−2.0 units of one another, as measured in $(MPa)^{1/2}$. Those skilled in the art may appreciate that the Hildebrand solubility parameter represents the square root of the cohesive energy density and provides a numerical estimate of the degree of interaction of selected materials.

Furthermore, it may be appreciated that luminescent standard may be chosen based on luminescent interactions with the oxygen sensitive luminescent colorant and/or core materials. For example, the luminescent standard may exhibit at least one excitation wavelength $\lambda_{exs}$ that may be relatively the same or different as at least one excitation wavelength of the luminescent colorant $\lambda_{exc}$. The luminescent standard may exhibit at least one emission wavelength $\lambda_{ems}$ that is different from that of the luminescent colorant $\lambda_{emc}$. Where other core materials may exhibit luminescent characteristics, the excitation wavelengths exhibited by the chosen luminescent standard and the chosen luminescent colorant may be different from excitation wavelength(s) exhibited by other core materials $\lambda_{exm}$.

Figure 3:
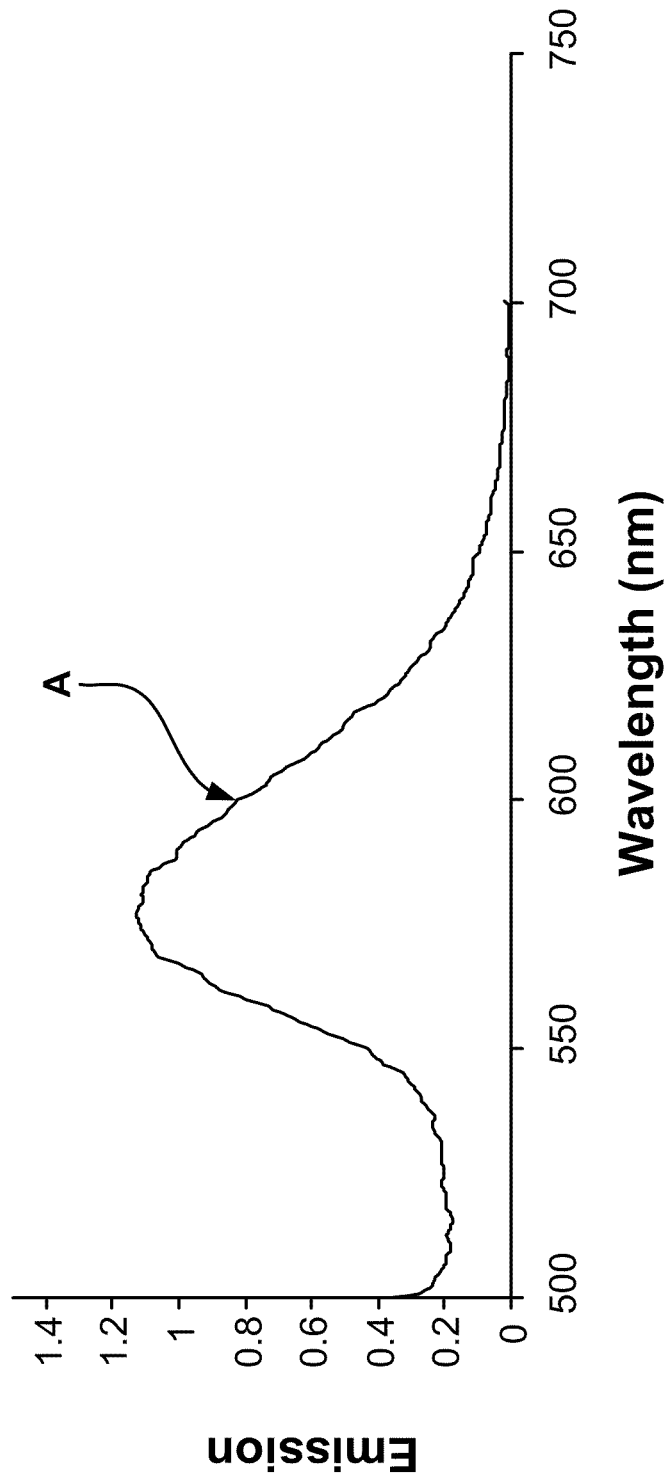
FIG. 3 illustrates the emission spectrum of an example of an oxygen sensitive luminescent colorant (tris(4,7-diphenyl-1,10-phenanthroline)ruthenium (II) bis(hexafluorophosphate) complex) "A" in canola oil excited at 485 nm.
Figure 4:
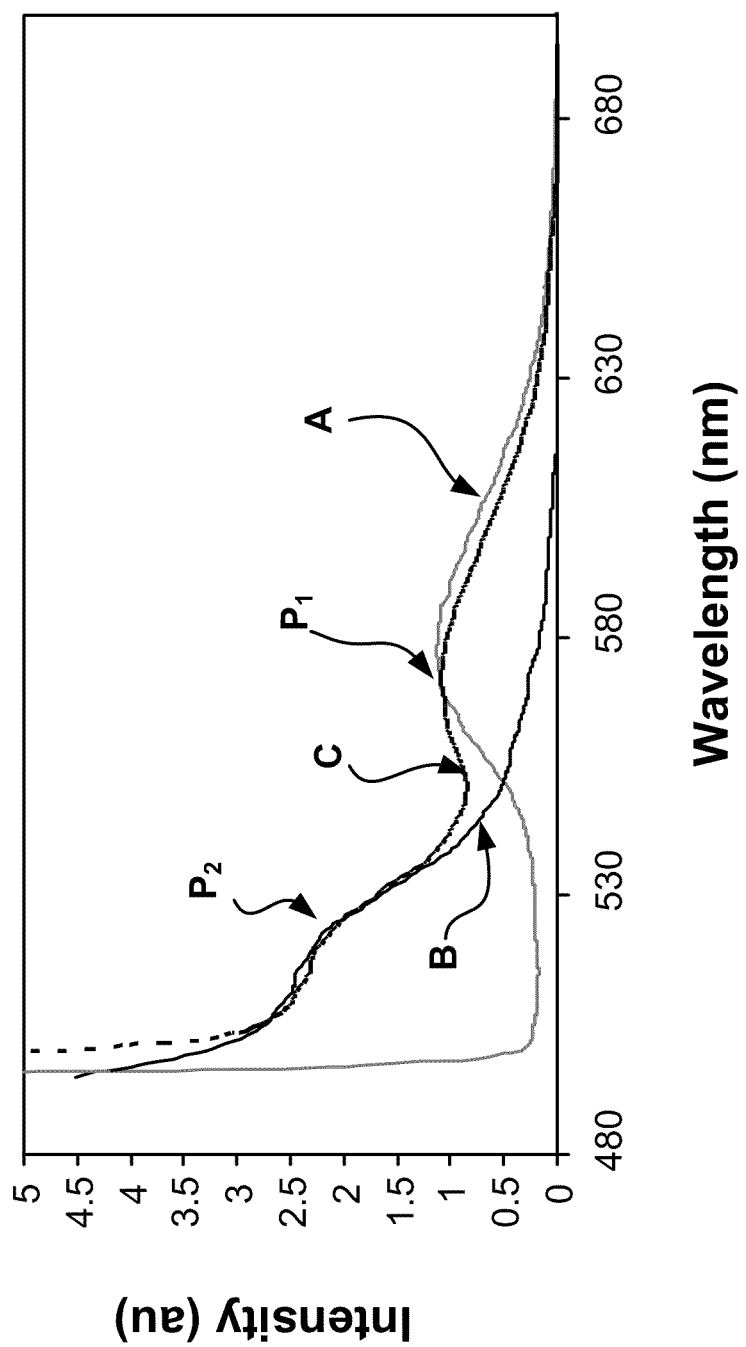
FIG. 4 illustrates the emission spectrum of an example of the oxygen sensitive luminescent colorant illustrated in FIG. 3, an emission spectrum of a luminescent standard and an emission spectrum of a mixture of both the oxygen sensitive luminescent colorant and the luminescent standard.

For example, FIG. 3 illustrates the emission spectrum of an example of an oxygen sensitive luminescent colorant (tris(4,7-diphenyl-1,10-phenanthroline)ruthenium (II) bis(hexafluorophosphate) complex) "A" in canola oil excited at 485 nm. FIG. 4 illustrates the emission spectrum of the oxygen sensitive luminescent colorant (tris(4,7-diphenyl-1,10-phenanthroline)ruthenium (II) bis(hexafluorophosphate) complex) "A", an example of a luminescent standard (DC108GY available from Angstrom Technologies) "B" and a combination of the luminescent standard with the oxygen sensitive luminescent colorant in canola oil excited at 485 nm "C". As can be seen, the combination of the oxygen sensitive luminescent colorant with the luminescent standard (curve "C") exhibited similar peak intensities of the individual oxygen sensitive luminescent colorant "$P_1$" and the luminescent standard "$P_2$." It may be observed that the combination may exhibit relatively slight shifts in the peak intensities and/or a shift in the wavelength where peak intensity is observed.

In addition, the luminescent standard may be present in the range of 50 ppm or less, including all values and increments therein, such as in the range of 1 ppm to 50 ppm. Examples of luminescent standards may include sulfonated coumarin dyes, sulfonated rhodamine dyes, sulfonated xanthene dye, sulfonated cyanine dyes, quantum dots, fluorescein, fluorescein derivatives, and/or combinations thereof.

Microcapsules including core materials with the luminescent colorant and the luminescent standard may be formed utilizing a number of techniques, such as coacervation, centrifugal extrusion, fluidized bed, spray drying, interfacial polymerization, reverse phase interfacial polymerization, etc. Once formed the capsules may be treated with a post-treatment process. The treatments may alter oxygen permeability or improve mechanical stability.

For example, the microcapsules may be formed by complex coacervation, which may be understood as when two or more oppositely-charged macromolecular colloids are used to form an aqueous solution, which may then be separated into two liquid phases. The first phase, called the coacervate, may include the colloid droplets, and the other liquid phase, called the equilibrium liquid, may include an aqueous solution of the coacervating agent. The core material may include oil based media, such as various organic oils, e.g., vegetable oils, or mineral oils and may be dispersed into a number of droplets through the solution.

Coacervation of the colloids around oil based core materials dispersed within the equilibrium liquid may occur at temperatures greater than the gelation temperature $T_{gel}$ of the colloid materials and may be triggered by, for example, a change in temperature, addition of an acid, or addition of water. The gelation temperature may be understood as the temperature above which a gel will not form or, in other words, the temperature at or below which the viscosity of the colloids may increase and form a substantially infinite polymer network. It may be appreciated that the gelation temperature may be affected by the concentration of the colloid, the solvent, and other factors. The mixture may be allowed to cool, allowing for a gel to form around the core material, creating microcapsules. The microcapsules may be post-treated by a number of processes including cross-linking, clay soaking and layer-by-layer (LBL) formation.

In one example, a first colloidal precursor, such as gelatin (mammalian or non-mammalian) or agar, may be added to a first solvent, such as water, forming a solution. The first colloidal precursor may be present in the solvent in the range of 0.1 to 5.0% by weight of the precursor to the first solvent/precursor mixture, including all values and increments therein. The solution may be maintained at a temperature that is higher than the gelation temperature $T_{gel}$ of the first colloidal precursor, such as greater than 50° C., including all values and increments in the range of 50° C. to 200° C. However, it may be appreciated that the temperature may be altered or varied, depending on the colloids or core materials utilized.

The core material may then be added to the solution and dispersed into the solution, forming a number of droplets or domains in the solution. The domains may have an average diameter (or largest linear dimension) of less than 100 μm, including all values and increments in the range of 0.1 μm to less than 100 μm. In addition, the core material may be present at a ratio in the range of 3:1 to 5:1 core material to first colloidal precursor by weight, including all values and increments therein.

A second colloidal precursor may then be added, such as carboxymethylcellulose, gum arabic or sodium hexametaphosphate. It may be appreciated that the second colloidal precursor may exhibit an opposite charge than the first colloidal precursor. The second colloidal precursor may be present in the range of 10 to 30% by weight of the combination of the first and second colloidal precursors, including all values and increments therein. The second colloidal precursor may be added in a second solution, wherein the solution may include in the range of 1 to 10% of the second colloidal precursor.

The pH may then be altered, such as by the addition of an appropriate acid or base. In one example, the pH may be lowered or adjusted in the range of 4.5 to 5.0 pH. The reaction mixture may then begin to cool and gels may begin to form. Once cooled to room temperature, the capsules may then be subjected to a post-treatment process. The capsules may then settle and separated from the supernatant and washed. It may be appreciated that the processes may occur under an inert atmosphere, which may prevent the oxidation of the core material. Exemplary inert atmospheres may include $N_2$ or Ar gas.

Examples of post treatment processes may include additional cross-linking, clay soaking, and layer by layer (LBL) formation utilizing various polycations and/or polyanions. It may be appreciated that more than one post treatment processes may be utilized as well. For example, the microcapsules may be treated with additional crosslinking and then LBL formation.

For example, additional cross-linking with crosslinking agents may be facilitated by mixing the microcapsules in a solution including a crosslinking agent. The solution may include 5 to 50% of the crosslinking agent, including all values and increments therein. The microcapsules may be crosslinked for 1 minute to 20 hours, including all values and increments therein, such as in the range of 2 hours to 20 hours, 4 hours to 12 hours, etc. In some examples, gelatin capsules may be crosslinked with gluteraldehyde or transglutaminase.

In clay soaking, the microcapsules may be soaked in a solution of exfoliated clay. Such clays may include kaolinite, betonite, smectite, illite or chlorite clays. The microcapsules may be soaked for a few minutes to 20 hours, including all values and increments therein, such as 2 hours to 15 hours, 12 hours, etc. Clay soaking may be utilized alone or in combination with both crosslinking and LBL formation. In some examples, clay soaking may be performed before other post-treatment processes and in other examples, it may be performed after other post-treatment processes.

In layer by layer formation (LBL), layers of polycations, polyanions or combinations thereof may be formed on the microcapsules surface. Polycations may include, for example, chitosan and polyanions may include, for example, clay or alginate. Once microcapsule formation is completed, excess liquid may be removed from the microcapsules such as through centrifuging and decanting of the supernatant The LBL process may include dispersing the microcapsules into pH 7 buffer and removing the microcapsules from the buffer, such as by centrifuging and decanting. The microcapsules may then be dispersed in a buffer having a pH of less than 7, such as, for example 4, which may include either polycations or polyanions, allowed to soak for a given period of time and then removed from the buffer. The microcapsules may again be dispersed into pH 7 buffer and again the capsules may be removed from the buffer, such as by centrifuging and/or decanting. To provide an additional layer, the microcapsules may be dispersed in a buffer having a pH of less than 7, such as, for example 4, which may include either polycations or polyanions, allowed to soak and then may be removed from the buffer. The method may be repeated a number of times while, for example, alternating the ionic layers. Similarly, LBL formation may be performed in combination with the other post-treatment processes, such as after crosslinking but before clay soaking; after crosslinking and clay soaking, etc.

Once the microcapsules are formed, they may be provided in solution or in dry form. To determine the oxidation of the core materials, the luminescence of the microcapsules may be monitored and determined periodically (at times $t_0$ and $t_1$) and a ratio of the luminescent standard to the oxygen sensitive luminescent colorant may be examined and compared to previous measurements. In one example, the luminescence may be measured by a spectrometer. A ratio between the luminescent standard and the oxygen sensitive luminescent colorant may be determined and the degree of oxidation may be gauged.

It may also be appreciated that the above may pertain, not only to oxygen sensitive ingredients and luminescent colorants but also to ingredients and corresponding luminescent colorants that may be sensitive to other environmental components. Such environmentally sensitive ingredients and luminescent colorants may include those that may exhibit chemical or physical changes upon exposure to one or more of moisture, a particular gas (such as oxygen, carbon dioxide, carbon monoxide etc.), a particular solvent (such as aqueous solvents, hydrocarbon based solvents, etc.), variations in pH and/or other particular substances that may adversely affect the activity of an ingredient contained within a microcapsule. An example of water sensitive luminescent colorants includes, but is not limited to, N,N'-dimethyl-N-(iodoacetyl)-N'-(7-nitrobenz-2-oxa-1,3-diazol-4-yl)ethylenediamine (IANBD amide), and an example of pH sensitive luminescent colorants includes, but is not limited to, SNARF-4F 5-(and -6)-carboxylic acid, both available from Invitrogen. The environmentally sensitive luminescent colorant may, therefore, be chosen on the basis described above and used in combination with an appropriately selected luminescent standard as described above. For example, the luminescent colorant may be chosen on the basis that an ingredient is sensitive to a given environment, i.e., a particular substance which the microcapsules may be exposed. The luminescent standard may be chosen based on its relative lack of sensitivity to such environment.

EXAMPLES

The following examples are presented for illustrative purposes only and therefore are not meant to limit the scope of the disclosure and claimed subject matter attached herein.

Various microcapsule formulations were provided using complex coacervation, in-situ polymerization and the formation of micelles. The oxygen stability (i.e., as indicated by the oxidation of the oxygen sensitive luminescent colorant) of the various microcapsule formulations was tested both in aqueous slurries and as dry paste by measuring the luminescence (i.e., luminescent signals) of the microcapsules over a given period off time by spectrophotometer analysis.

Core Material

The standard core material was produced by combining canola oil with up to 20 ppm of oxygen sensitive fluorescent dye, a tris(4,7-diphenyl-1,10-phenanthroline)ruthenium (II) bis(hexafluorophosphate) complex, and up to 20 ppm of an inert luminescent standard.

Microcapsules Formed by Complex Coacervation

A number of microcapsules were formed by complex coacervation by dissolving 10 grams of 300 Bloom Type A gelatin in 400 mL of deionized water at 60° C. Then, 40 grams of core material was homogenized into the gelatin solution to form droplets less than 100 μm in diameter. 20 mL of 5% sodium hexametaphosphate solution was added to the gelatin solution. The pH of the solution was then lowered to approximately 4.8 upon the addition of 10% acetic acid. The reaction mixture was then allowed to cool to room temperature, followed by post-treatment (described below). The capsules were then allowed to settle, were separated from the supernatant and washed three times with fresh deionized water. All steps were carried out under an inert gas $N_2$ or $Ar_2$ to prevent oxidation. Fish gelatin microcapsules were also produced.

Microcapsules Formed by In-Situ Polymerization

Microcapsules including a urea-formaldehyde shell were prepared by mixing 50 mL of a 10% ethylene maleic anhydride solution with 2.5 grams of urea and 0.25 grams of resorcinol at room temperature. Approximately 30 mL of ultra pure water was added to the mixture. The pH of the mixture was then raised to 3.7 with a concentrated solution of NaOH. 25 g of core material was emulsified into the aqueous solution and then 6.7 g of formaldehyde was added. The system was heated to 60° C. for at least 2 hours. The microcapsules were isolated for testing once the solution cooled. The solutions were purged and reacted under inert conditions during processing to prevent oxidation.

Post Treatment

After the various microcapsules were produced, a number of post-treatment processes were performed using three methods of post-treatment alone or in combination. The first method included cross-linking the microcapsules produced by complex coacervation. Two cross-linking agents, gluteraldehyde and transglutaminase, were separately utilized. A first 50 gram batch of gelatin microcapsules were crosslinked with 5 mL of a 25% gluteraldehyde solution over a time period of 4 (for glut-lite samples) to 12 hours for the remainder of the samples crosslinked with gluteraldehyde. A second batch was cross-linked by soaking microcapsules in 0.1% (w.t.) transglutaminase overnight.

A second method of post-treatment included depositing clay onto the surface of the microcapsules. The microcapsules were soaked in a solution of exfoliated clay for 12 hours either before or after other post treatment processes.

The third method of post treatment included layer by layer development on the surface of the microcapsules. First a dispersion of microcapsules were centrifuged and the supernatant was decanted. The microcapsules were then redispersed into a pH 7 buffer. Then the capsules were centrifuged and the supernatant was decanted. The capsules were then redispersed into a buffer of 4 pH containing alginate or clay. The capsules were centrifuged and decanted again, redispersed in a 7 pH buffer and again centrifuged and decanted. The capsules were then redispersed in a pH 4 buffer including chitosan and centrifuged and decanted. Dispersal of the capsules in a 7 pH buffer was again alternated by dispersal into a 4 pH buffer including either the polyanion or polycation followed by centrifuging and decanting until two additional layers of the polyanion and polycation were formed over the microcapsule.

Table 1 below summarizes the microcapsule formulations and post-treatments. The various order in which post-treatment occurred where more than one post-treatment process was applied is also described in the table below for each sample.

TABLE 1

Sample Formulations

| Sample Number | Shell | Cross-linking | Shell Treatment |
|---|---|---|---|
| 1 | 300 Bloom Type A Gelatin | None | None |
| 2 | 300 Bloom Type A Gelatin | Gluteraldehyde | None |
| 3 | 300 Bloom Type A Gelatin | Transglutaminase | None |
| 4 | Urea-Formaldehyde | None | None |
| 5 | Fish Gelatin | Transglutaminase | None |
| 6 | 300 Bloom Type A Gelatin | None | Microcapsules were soaked in a solution of exfoliated kaolin clay |
| 7 | 300 Bloom Type A Gelatin | None | Microcapsules were soaked in a solution of exfoliated sodium bentonite clay |
| 8 | 300 Bloom Type A Gelatin | Transglutaminase | Microcapsules were soaked in a solution of exfoliated kaolin clay before crosslinking |
| 9 | 300 Bloom Type A Gelatin | Transglutaminase | Microcapsules were soaked in a solution of exfoliated sodium bentonite clay before crosslinking |
| 10 | 300 Bloom Type A Gelatin | Transglutaminase | LBL formation was used to deposit a layer of clay and a layer of chitosan after crosslinking |
| 11 | 300 Bloom Type A Gelatin | Transglutaminase | LBL formation was used to deposit two layers of clay and a layer of chitosan in between after crosslinking |
| 12 | 300 Bloom Type A Gelatin | None | LBL formation was used to deposit 5 layers of alternating bentonite clay and chitosan |
| 13 | 300 Bloom Type A Gelatin | None | LBL formation was used to deposit 5 layers of alternating bentonite clay and chitosan, with additional soak time between the layers |
| 14 | 300 Bloom Type A Gelatin | None | LBL formation was used to deposit ten alternating layers of clay and chitosan |
| 15 | 300 Bloom Type A Gelatin | Transglutaminase | LBL formation was used to deposit five alternating layers of clay and chitosan after crosslinking |

TABLE 1-continued

Sample Formulations

| Sample Number | Shell | Cross-linking | Shell Treatment |
|---|---|---|---|
| 16 | 300 Bloom Type A Gelatin | Transglutaminase | LBL formation was used to deposit five alternating layers of clay and chitosan with additional soak time in between the layers after crosslinking |
| 17 | 300 Bloom Type A Gelatin | Transglutaminase | LBL formation was used to deposit ten alternating layers of clay and chitosan after crosslinking |
| 18 | 300 Bloom Type A Gelatin | Transglutaminase | First the microcapsules were soaked in bentonite and then LBL formation was used to deposit ten alternating layers of clay and chitosan before crosslinking |
| 19 | 300 Bloom Type A Gelatin | Transglutaminase | First the microcapsules were soaked in kaolin and then LBL formation was used to deposit ten alternating layers of clay and chitosan before crosslinking |

Oxygen Barrier Analysis

Stability experiments were carried out on microcapsule aqueous slurries, wherein the microcapsules were prepared as described in the samples above. In the following stability analysis, six batches of microcapsule slurries were formed by dispersing approximately 4 grams of microcapsules in 40 mL of water.

A first stability tests were performed on the microcapsules prepared as described in example 1, which were then, as described above, dispersed in water. A first set (three batches) of microcapsule slurries were maintained under an inert atmosphere ($N_2$ or Ar) through the stability testing and labeled the control. Another set (three batches) of microcapsule slurries were agitated at room temperature and exposed to air. The air exposed capsules were placed in a beaker with a magnetic stir bar to continuously agitate the solution. Periodically, 0.2 mL of microcapsules was collected from each set of samples and the fluorescence of the samples was measured.

The fluorescence spectra of the core materials were collected with a Perkin Elmer LS50B Luminescence Spectrometer. Fluorescence of the microcapsule samples was monitored with a Beckman Coulter DTX880 Multimode Detector. Microcapsule samples were excited at 485 nm and measurements were made at 535 nm and 625 nm. A ratio of the luminescent standard signals and the oxidation sensitive luminescent colorant signals were used to quantify core material oxidation.

Figure 5:
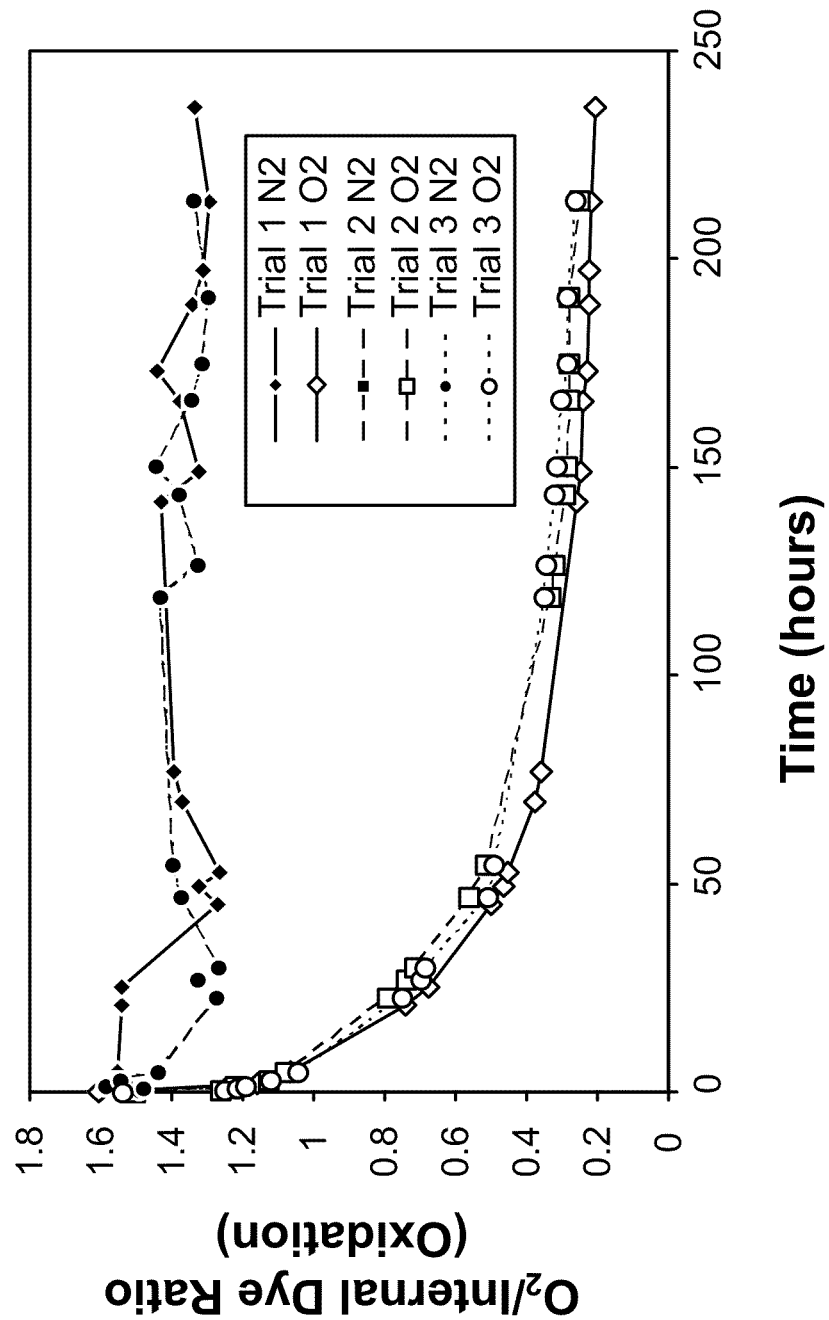
FIG. 5 illustrates the ratio of luminescent intensity over a period of time between the oxygen sensitive luminescent colorant and the luminescent standard in noncrosslinked microcapsules.

As illustrated in FIG. 5, the three batches (labeled as Trials 1-3 O2) exposed to air exhibited a 90% drop in luminescent signal over 200 hours, indicating oxidation of the core materials. The purged samples (those maintained under an inert atmosphere) (labeled as Trials 1-3 N2) remained relatively stable over the 200 hour time period. Optical micrographs of the microcapsules before and after the study revealed that the capsules agitated under air fell apart and were not present at the end of the 200 hour period. Thus, the detected luminescent signal for the microcapsules agitated in air did not reflect the oxygen barrier properties of the gelatin; as the capsules fell apart, the core material was exposed to the surrounding environment resulting in relatively rapid oxidation. Without being bound to a particular theory, it appears the agitation of the air exposed capsules using the stir bar caused rupture of the capsules via shear forces. Accordingly, testing of the capsules exposed to air was modified to agitate in a shaker to avoid the introduction of shear forces. However, these capsules fell apart as well.

Figure 6:
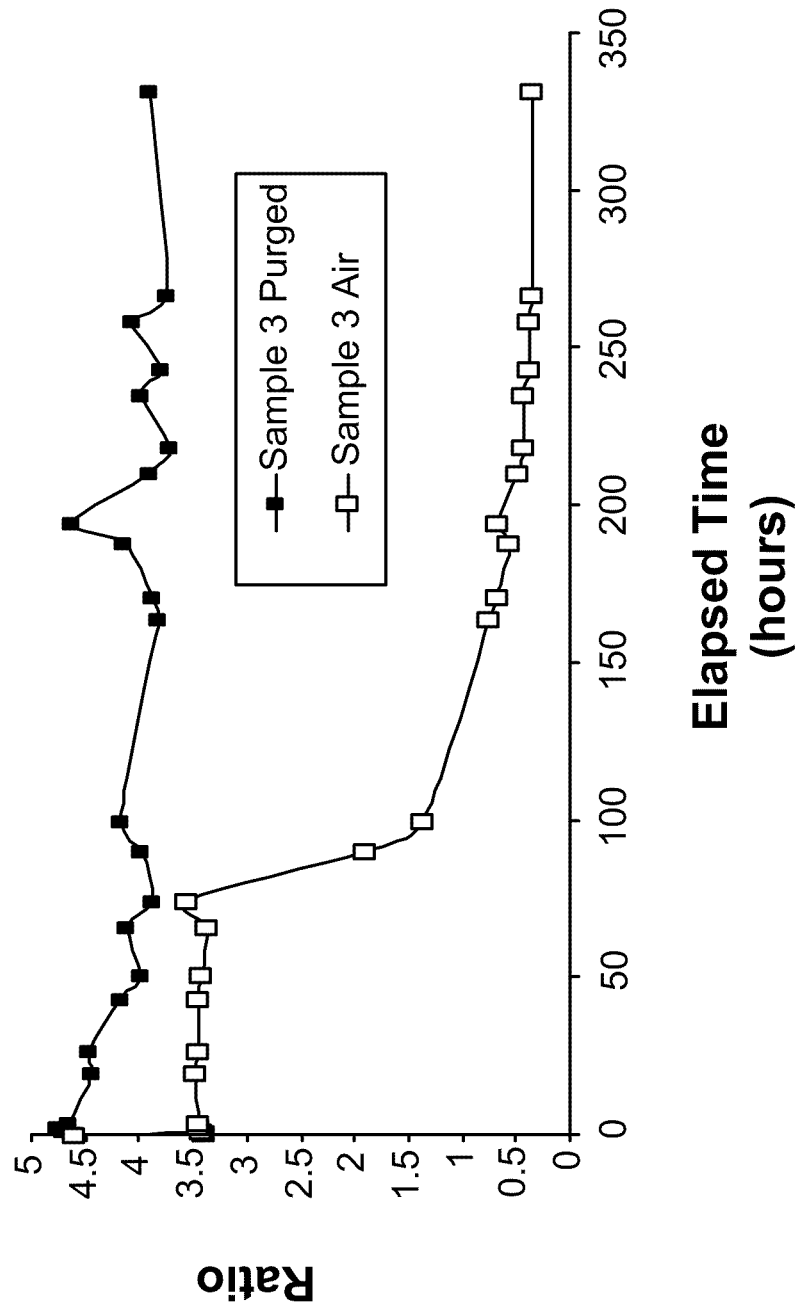
FIG. 6 illustrates the ratio of luminescent intensity over a period of time between the oxygen sensitive luminescent colorant and the luminescent standard in transglutaminase crosslinked microcapsules.

Crosslinking methods, such as in samples 2 and 3, were utilized to prevent the breakdown of the capsules. Gluteraldehyde was investigated as a crosslinking agent (sample 2) in stability studies, as outlined above (i.e., 4 grams of microcapsules were mixed with 40 mL of water and batches were agitated in both inert and air atmospheres maintained at 25° C.) and the luminescence was measured over a course of 200 hours. However, relatively low luminescent intensity was exhibited and relatively little signal change was observed through the course of the trial. Without being bound to a particular theory, it appears that cross-linking with gluteraldehyde caused some degree of change in microcapsule color, which blocked at least a portion of the excitation and/or emission light. Transglutaminase was then utilized as a crosslinking agent (sample 3). Microcapsules from sample 1 were crosslinked overnight with 0.1% transglutaminase (with respect to gelatin weight). A portion of the crosslinked microcapsules were agitated in air and another portion of the crosslinked microcapsules were agitated in an inert environment. FIG. 6 illustrates the results of the stability analysis, which occurred at a temperature of 25° C. over a period of approximately 325 hours. The ratio of the oxygen sensitive luminescent colorant to the luminescent standard remained relatively constant for both samples for up to approximately 72 hours. However, after this initial time period, the measured luminescence for the samples exposed to air dropped in a relatively rapid manner. The relatively rapid drop appears to have corresponded with a mechanical breakdown of the microcapsules. It is noted that the samples maintained in the inert atmosphere did not exhibit a similar deterioration and breakdown.

Figure 7:
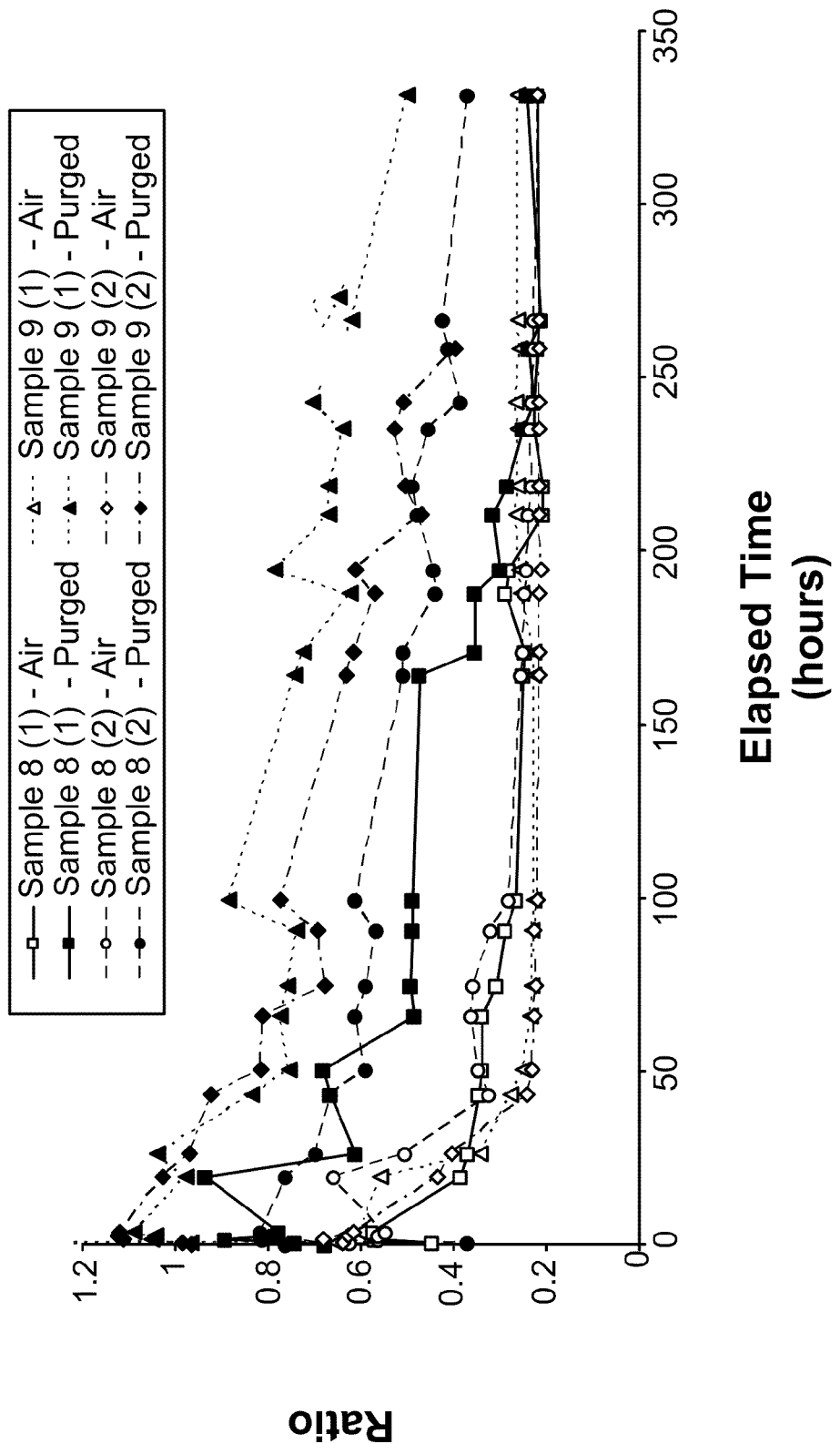
FIG. 7 illustrates the ratio of luminescent intensity over a period of time between the oxygen sensitive luminescent colorant and the luminescent standard in clay soaked microcapsules.

Clay soaked microcapsules, crosslinked with transglutaminase, were then tested, such those illustrated in samples 8 and 9. After forming the microcapsules as in sample 1, the microcapsules were soaked in either kaolin or bentonite clay and then crosslinked. Oxygen stability tests were performed on each sample set in both inert and air exposed atmospheres and the luminescence of the microcapsules were measured at various intervals. The results of the testing is illustrated in FIG. 7, which demonstrates that the purged samples exhibit a higher luminescent ratio and a slow decay in the ratio, whereas the air exposed samples illustrated a relatively sharp decline in luminescent ratio and appeared to be saturated with oxygen within three days. Optical microscopy of the capsules indicated that the capsules fell apart.

Figure 8:
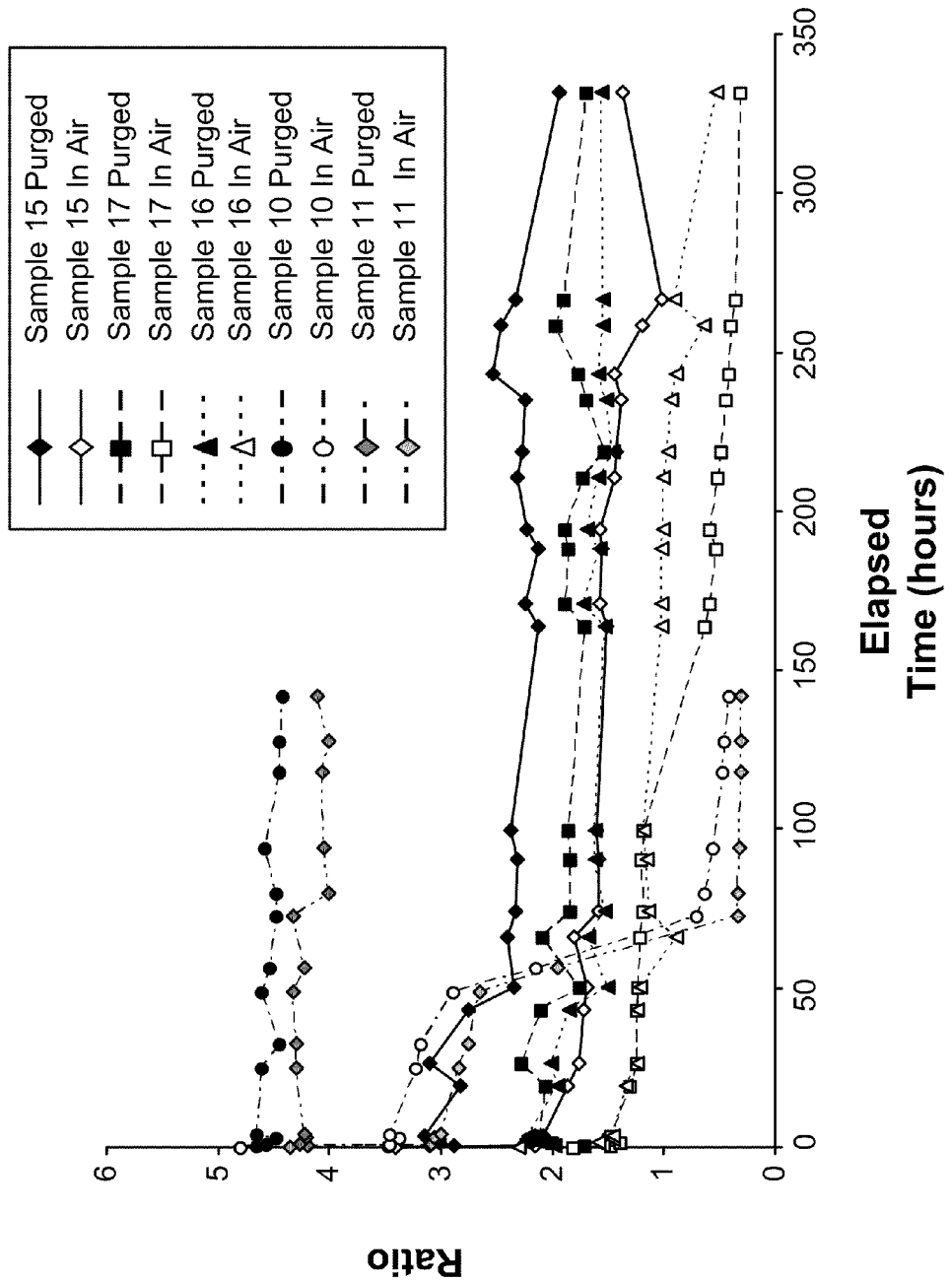
FIG. 8 illustrates the ratio of luminescent intensity over a period of time between the oxygen sensitive luminescent colorant and the luminescent standard in microcapsules including layer by layer formation.

Microcapsules were then provided that were crosslinked and provided with ionic layers of clay and chitosan through LBL formation after crosslinking as described in samples 10, 11, 15, 16 and 17. Various layer configurations were examined, including 2 layers, 3 layers, 5 layers and 10 layers (samples 10, 11, 15, and 17, respectively). In addition, a 5 layer configuration, wherein the layers were formed using additional soak time (sample 16) was examined. Each configuration was tested in both inert and air exposed atmospheres and the luminescence was measured periodically. FIG. 8 illustrates that the purged/inert samples exhibited relatively higher fluorescent ratios with some decay in intensity over time. With respect to the samples exposed to air, the two layer and three layer samples fell apart after approximately two days and exhibited a sharp decay in intensity. The five to ten layer samples exhibited a relatively less significant decrease in intensity and the microcapsules remained intact over the course of testing. The 5 layered long soaked samples exhibited a relatively lower intensity than the base 5 layer samples; however, the rate of decrease appeared to be relatively similar to the base 5 layer samples. The 10 layer samples exhibited a relatively higher rate of oxidation between 100 and 150 hours.

Figure 9:
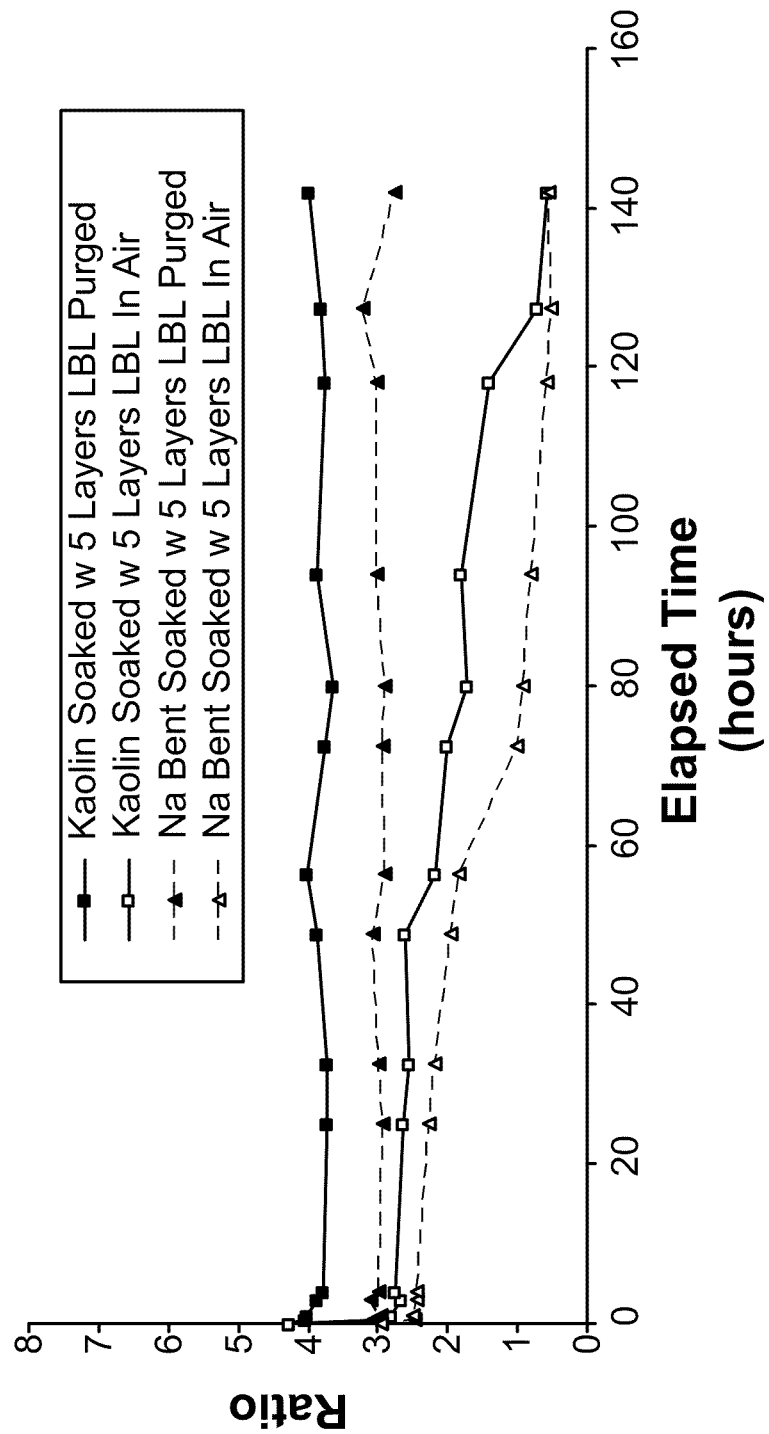
FIG. 9 illustrates the ratio of luminescent intensity over a period of time between the oxygen sensitive luminescent colorant and the luminescent standard in clay soaked microcapsules including layer by layer formation.

Another study was performed with microcapsules that included the addition of five polyanionic or polycationic layers to microcapsules by layer by layer formation that had already been soaked in either kaolin or bentonite clay. Once again, the microcapsules were tested for oxygen stability and the luminescence was measured periodically over the course of testing. The results of the stability testing are illustrated in FIG. 9. The purged/inert microcapsules were relatively stable over the course of testing, whereas the air exposed microcapsules exhibit a decrease in intensity after approximately 2 days and at the end of 140 hours disintegrated, as confirmed by optical microscopy.

Dry Capsule Testing

Figure 10:
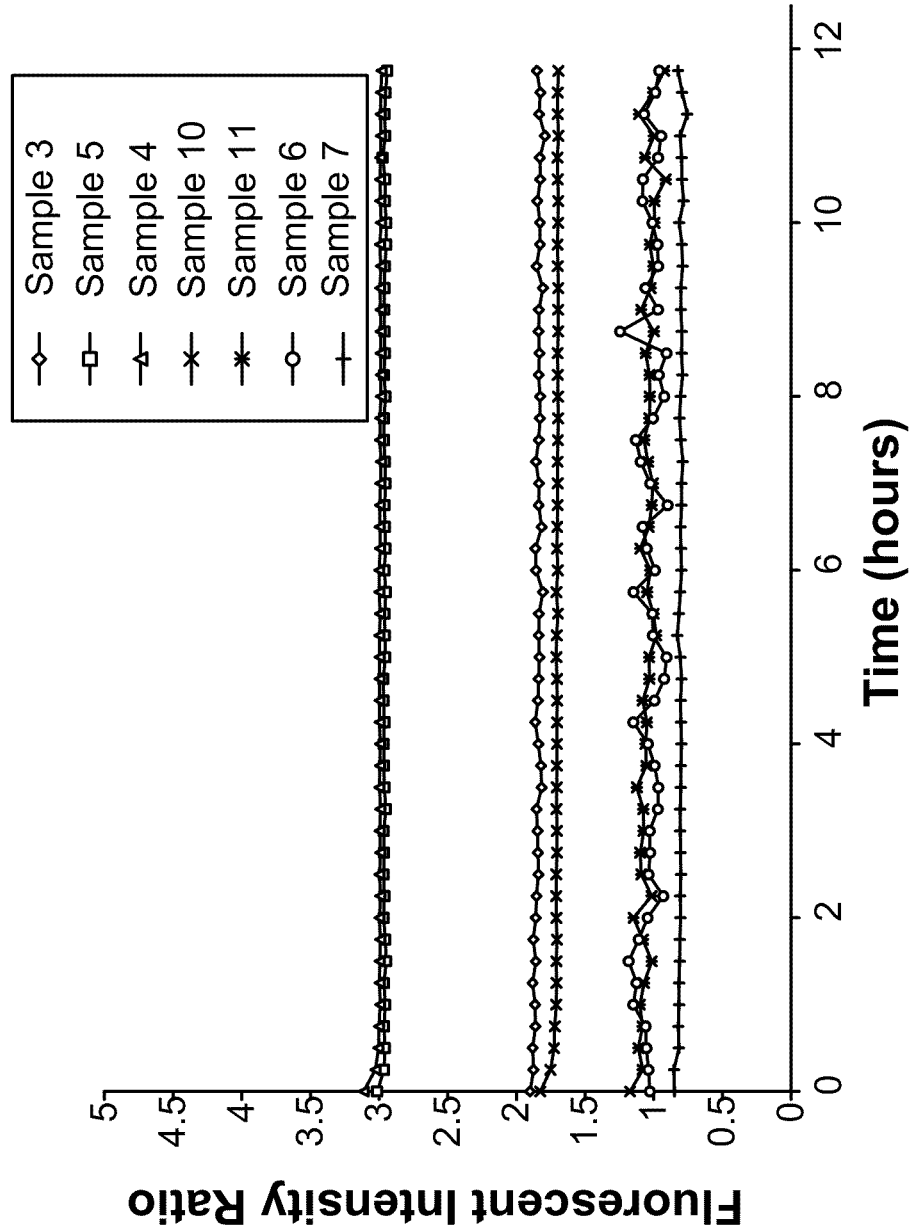
FIG. 10 illustrates the ratio of luminescent intensity over a period of time between the oxygen sensitive luminescent colorant and the luminescent standard in a variety of dried microcapsule samples.

Dry microcapsule samples of transglutaminase crosslinked microcapsules (sample 3), microcapsules formed from fish gelatin (sample 5), microcapsules formed from urea formaldehyde (sample 4), 2 LBL formation treated microcapsules (sample 10), 3 LBL treated microcapsules (sample 11), microcapsules soaked in kaolin clay (sample 6) and microcapsules soaked in bentonite (sample 7) were prepared by centrifuging 50 ml of microcapsule slurry at 3200 rpm for 10 minutes. The precipitate was placed into the wells of a 96 well plate. The plate and microcapsules were dried in a vacuum overnight at 40° C., followed by fluorescence kinetic measurements, discussed further below. The microcapsules were exposed to air and stored in the analyzer between luminescent sampling. Each cell was analyzed in a 4×4 array to produce 16 measurements within the cell. The measurements were averaged and FIG. 10 illustrates the averaged results. The slope of the line was used to characterize the oxidation of the core material, under the assumption was made that the oxygen diffusion rate into the microcapsules was linear.

Figure 11:
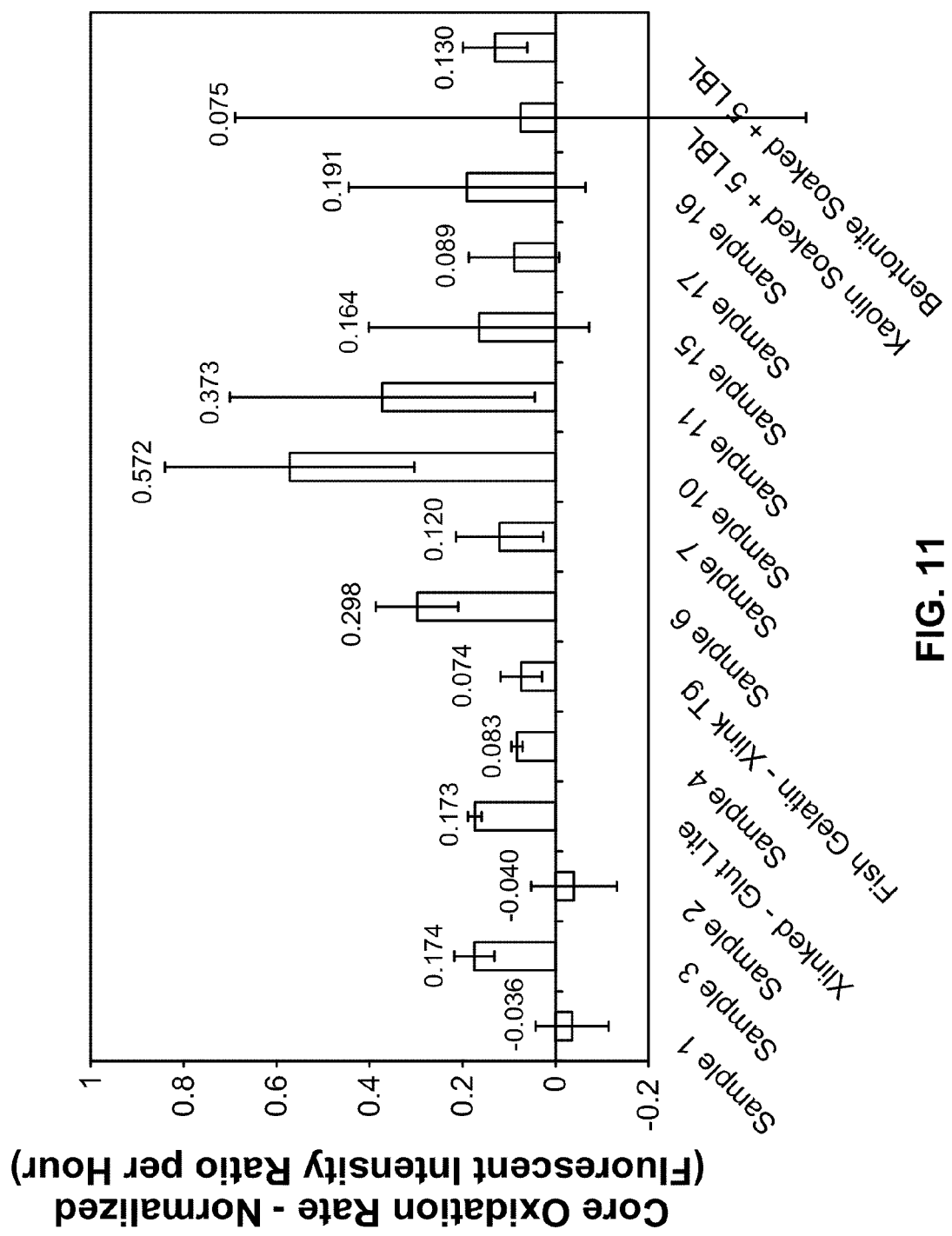
FIG. 11 illustrates the ratio of luminescent intensity over a period of time between the oxygen sensitive luminescent colorant and the luminescent standard in a variety of dried microcapsule samples.

Furthermore, each sample (samples 1-17 in Table 1 above) prepared in slurry was dried and oxygen stability tested as a dry powder. Three samples of each composition were tested twice for 12 hours at 40° C. resulting in 6 data sets for each composition. The normalized averages of these sets are illustrated in FIG. 11, which also illustrates the standard deviation. As can be seen in the figure, the non-crosslinked samples (sample 1) offered relatively better protection from oxygen than the remainder of the formulations; however, the mechanical stability of this formulation may be problematic (i.e. see FIG. 5). The gluteraldehyde crosslinked samples (sample 2) offered what appeared to be relatively good protection from oxygen as well.

In comparison, an alternate gelatin (fish gelatin crosslinked with transglutaminase) and a non-gelatin sample (urea-formaldehyde) (sample 4) were examined. The crosslinked fish gelatin exhibited a relatively better barrier performance than the crosslinked transglutaminase samples and the lightly crosslinked gluteraldehyde samples. The poly(urea formaldehyde) exhibited relatively stable fluorescence and yielded oxygen barrier performance analogous to that of the fish gelatin.

The soaking of the microcapsules in the various clays (samples 6 and 7) demonstrated that the benefits may be somewhat negligible over the use of other methods. However, the bentonite soaked samples exhibited better oxygen stability over the kaolin clay samples.

In addition, the sampling indicated that increasing the number of layers applied by LBL formation improved the oxygen barrier performance of the microcapsules, despite relatively large deviations. It is noted that allowing the microcapsules to soak in the ionic solution for longer time periods (sample 16) did not necessarily result in better oxidation stability. In addition, the 2 layer sample, (sample 10) exhibited relatively poor oxygen barrier performance. Without being bound to any particular theory, it appears that the gelatin hydrates and swells, allowing for the penetration of electrolytes into the gelatin shell. The penetration and plasticization may decrease the oxygen barrier performance of the gelatin.

The formulations that were soaked in clay, crosslinked with transglutaminase and then provided with 5 alternating layers of clay and chitosan by LBL formation exhibited relatively better oxygen barrier performance that the 5 LBL microcapsules without prior clay soaking. In addition, the bentonite soaked, crosslinked and clay layered sample, exhibited relatively similar oxygen barrier performance as the sample without bentonite soaking (sample 15).

Finally, relatively large performance enhancements were exhibited by the 10 layer LBL formation sample (sample 17) and the crosslinked, kaolin soaked, 5 layer LBL formation sample. However, the relatively large degree of error is noted. In addition, it is also noted that LBL formation may be relatively complex and time-consuming.

Micelles

Micelles were then prepared using the same standard core material described above. 80 grams of Tween 80 was placed in a closed system purged with Ar and was stirred. 12 grams of the canola oil and colorant mixture was slowly added to the Tween via syringe to form a homogenous solution. Then 200 ml of ultra pure water was added drop wise for approximately 1 hour while stirring. The solution was stirred under Ar at room temperature for 72 hours. The average diameter of the micelles were 255 nm.

Figure 12:
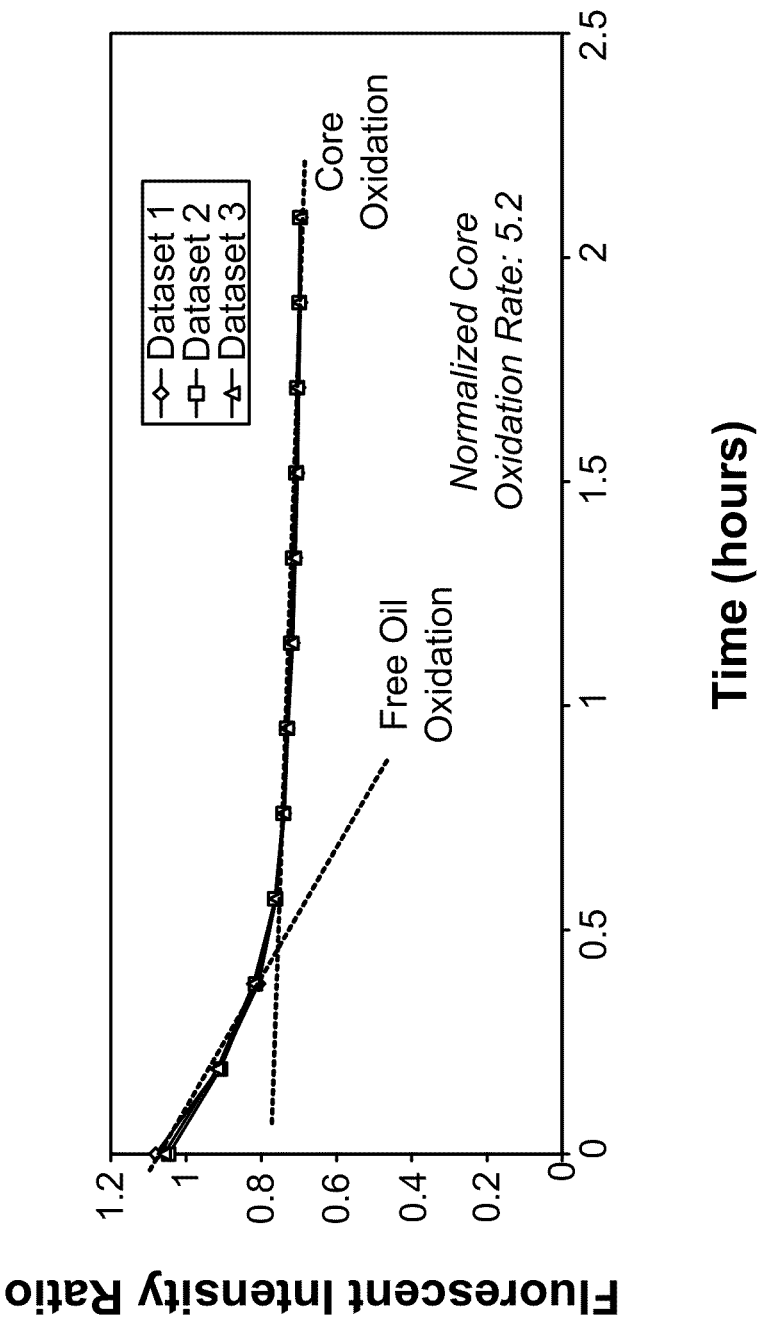
FIG. 12 illustrates the ratio of luminescent intensity over a period of time between oxygen sensitive luminescent colorant and the luminescent standard encapsulated in micelles measured over a period of time.

The micelle solution was periodically tested (i.e., the luminescence was measured) as a slurry over a 2 hour period to generate data for calculation of an oxidation rate. FIG. 12 illustrates the results. It appears that the core material oxidation was divided into two mechanisms as illustrated in FIG. 12, the first being free oil oxidation and the second being the oxidation of encapsulated oil. As may be appreciated, and without being bound to any particular theory, unlike in complex coacervation or in-situ polymerization, micelles exhibit less than 100% encapsulation efficiency. Free unencapsulated oil was present in the solution and oxidized at a much faster rate than the encapsulated oil. Assuming linear oxidation, the normalized oxidation rate was determined to be 5.2, which appears to be about 5 times greater than the gelatin microcapsules.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. Microcapsules comprising
   a shell material;
   a core material, wherein said core material includes:
   i) an environmentally sensitive luminescent colorant present in the range of 1 ppm to 50 ppm which exhibits characteristics of an emitted wavelength bandwidth, a peak intensity for emission and a time for luminescence decay, one or more of said characteristics capable of changing upon exposure to a given environment;
   ii) a luminescent standard present in the range of 1 ppm to 50 ppm which exhibits characteristics of an emitted wavelength bandwidth, a peak intensity for emission and a time for luminescence decay, one or more of said characteristics do not change upon exposure to said given environment and wherein said luminescent standard is selected from one or more of the following: sulfonated coumarin dyes, sulfonated rhodamine dyes, sulfonated xanthene dye, sulfonated cyanine dyes, and quantum dots; and
   iii) an ingredient, wherein said ingredient includes one or more of the following: pharmaceuticals, flavorants, or attractants and wherein said environmentally sensitive luminescent colorant has a first rate of oxidation correlated with a second rate of oxidation of said ingredient; and
   iv) a hydrocarbon solvent; and
   one or more layers formed on the microcapsule surface selected from the group consisting of polyanions, polycations and combinations thereof,
   wherein said environmentally sensitive luminescent colorant and said luminescent standard are measurable through said shell without rupturing said microcapsules.

2. The microcapsules of claim 1, wherein said emitted wavelength bandwidth of said environmentally sensitive luminescent colorant is capable of changing or shifting in the range of +/−50 nm.

3. The microcapsules of claim 1, wherein said peak intensity for emission of said environmentally sensitive luminescent colorant is capable of shifting in the range of +/−50 nm.

4. The microcapsules of claim 1, wherein said time for decay of said environmentally sensitive luminescent colorant is capable of changing within +/−5 seconds.

5. The microcapsules of claim 1, wherein said environmentally sensitive luminescent colorant exhibits a first excitation wavelength $\lambda_{exc}$ and said luminescent standard exhibits a second excitation wavelength $\lambda_{exs}$, and said environmentally sensitive luminescent colorant exhibits a first emission wavelength $\lambda_{emc}$ and said luminescent standard exhibits a second wavelength $\lambda_{ems}$ which are different.

6. The microcapsules of claim 1, wherein said environmentally sensitive luminescent colorant and said luminescent standard exhibit a Hildebrand solubility values (δ) that are within +/−2.0 units of one another, as measured in $(MPa)^{1/2}$.

7. A method of forming microcapsules, comprising:
   mixing a hydrocarbon solvent, an environmentally sensitive luminescent colorant, a luminescent standard, and an ingredient wherein said ingredient includes one or more of the following: pharmaceuticals, flavorants, or attractants to form a core material, wherein said environmentally sensitive luminescent colorant exhibits characteristics of i) an emitted wavelength bandwidth, ii) a peak intensity for emission and iii) a time for luminescence decay, one or more of said characteristics capable of changing upon exposure to a given environment and wherein said environmentally sensitive luminescent colorant has a first rate of oxidation correlated with a second rate of oxidation of said ingredient and said luminescent standard exhibits characteristics of i) an emitted wavelength bandwidth, ii) a peak intensity for emission and iii) a time for luminescence decay, one or more of said characteristics do not change upon exposure to said given environment and said luminescent standard is selected from one or more of the following: sulfonated coumarin dyes, sulfonated rhodamine dyes, sulfonated xanthene dye, sulfonated cyanine dyes, and quantum dots; and
   encapsulating said core material in a shell material forming microcapsules by complex coacervation; and
   forming one or more layers on the microcapsule surface selected from the group consisting of polyanions, polycations and combinations thereof using layer by layer formation, wherein said environmentally sensitive luminescent colorant is present in the range of 1 ppm to 50 ppm and said luminescent is present in the range of 1 ppm to 50 ppm and said environmentally sensitive luminescent colorant and said luminescent standard are measurable through said shell without rupturing said microcapsules.

8. The method of claim 7, wherein said emitted wavelength bandwidth of said environmentally sensitive luminescent colorant is capable of changing or shifting in the range of +/−50 nm.

9. The method of claim 7, wherein said peak intensity for emission of said environmentally sensitive luminescent colorant is capable of shifting in the range of +/−50 nm.

10. The method of claim 7, wherein said time for decay of said environmentally sensitive luminescent colorant is capable of changing within +/−5 seconds.

11. The method of claim 7, wherein said environmentally sensitive luminescent colorant exhibits a first excitation wavelength $\lambda_{exc}$ and said luminescent standard exhibits a second excitation wavelength $\lambda_{exs}$, and said environmentally sensitive luminescent colorant exhibits a first emission wavelength $\lambda_{emc}$ and said luminescent standard exhibits a second wavelength $\lambda_{ems}$ which are different.

12. The method of claim 7, further comprising cross-linking said shell material.

13. The method of claim 7, further comprising soaking said microcapsules in clay.

14. The method of claim 1, wherein said luminescent standard and said luminescent colorant have Hildebrand solubility parameter values (δ) that are within +/−2.0 units of one another, as measured in $(MPa)^{1/2}$.

15. A method of identifying changes in a core material in a microcapsule due according to claim 1, to environmental exposure comprising:

(i) providing microcapsules including a core material whose environmental sensitivity is to be monitored, said microcapsule containing an environmentally sensitive luminescent colorant exhibiting a first set of luminescent characteristics and an environmentally insensitive luminescent standard exhibiting a second set of luminescent characteristics;

(ii) measuring the first and second set of luminescent characteristics of the microcapsules at a time $t_0$ and $t_1$ in a given environment;

(iii) examining the difference between the first and second sets of luminescent characteristics of said environmentally sensitive luminescent colorant and said luminescent standard;

(iv) identifying a change in said core material associated with the difference in luminescent characteristics identified in step (iii).

16. The method of claim 15, wherein said environmentally sensitive luminescent colorant exhibits characteristics of an emitted wavelength bandwidth, a peak intensity for emission and a time for luminescence decay, one or more of said characteristics capable of changing upon exposure to a given environment and said luminescent standard exhibits characteristics of an emitted wavelength bandwidth, a peak intensity for emission and a time for luminescence decay, one or more of said characteristics not changing upon exposure to said given environment.

17. The method of claim 15, wherein said environmentally sensitive luminescent colorant exhibits a first excitation wavelength $\lambda_{exc}$ and said luminescent standard exhibits a second excitation wavelength $\lambda_{exs}$, and said environmentally sensitive luminescent colorant exhibits a first emission wavelength $\lambda_{emc}$ and said luminescent standard exhibits a second wavelength $\lambda_{ems}$ which are different.

18. A method of identifying changes in an ingredient within a core material in a microcapsule according to claim 1, due to environmental exposure comprising:

(i) providing microcapsules including a core material and an ingredient whose environmental sensitivity is to be monitored, said microcapsule containing an environmentally sensitive luminescent colorant exhibiting a first set of luminescent characteristics and an environmentally insensitive luminescent standard exhibiting a second set of luminescent characteristics;

(ii) measuring the first and second set of luminescent characteristics of the microcapsules at a time $t_0$ and $t_1$ in a given environment;

(iii) examining the difference between the first and second sets of luminescent characteristics of said environmentally sensitive luminescent colorant and said luminescent standard;

(iv) identifying a change in said ingredient associated with the difference in luminescent characteristics identified in step (iii).

* * * * *